United States Patent
Cardineau et al.

(10) Patent No.: US 6,326,587 B1
(45) Date of Patent: Dec. 4, 2001

(54) APPARATUS FOR REMOVING AN INSULATING LAYER FROM A PORTION OF A CONDUCTOR

(75) Inventors: Yan Cardineau, Angleton; Mark M. Frankovich, Sugarland, both of TX (US)

(73) Assignee: Intermedics Inc., Angleton, TX (US)

( * ) Notice: Subject to any disclaimer, the term of this patent is extended or adjusted under 35 U.S.C. 154(b) by 0 days.

(21) Appl. No.: 09/365,353

(22) Filed: Jul. 30, 1999

Related U.S. Application Data (62) Division of application No. 08/744,239, filed on Nov. 5, 1996, now Pat. No. 5,935,465.

(51) Int. Cl.$^7$ .................................................. B23K 26/36
(52) U.S. Cl. ................................................... 219/121.68
(58) Field of Search ................ 219/121.68, 121.69, 219/121.85; 427/554, 555, 556; 264/400

(56) References Cited

U.S. PATENT DOCUMENTS

| | | | |
|---|---|---|---|
| 3,367,339 | 2/1968 | Sessions | 128/418 |
| 3,474,791 | 10/1969 | Bentov | 128/148 |
| 3,572,344 | 3/1971 | Bolduc | 128/418 |
| 3,596,662 | 8/1971 | Bolduc | 607/129 |
| 3,610,874 | 10/1971 | Gagliano | 219/121.6 |
| 3,953,706 | 4/1976 | Harris et al. | 219/121.6 |
| 4,106,512 | 8/1978 | Bisping | 128/418 |
| 4,327,747 | 5/1982 | Gold | 607/119 |
| 4,399,345 | 8/1983 | Lapharm et al. | 219/121.69 |
| 4,514,589 | 4/1985 | Aldinger et al. | 174/119 R |
| 4,559,951 | 12/1985 | Dahl et al. | 128/642 |
| 4,640,983 | 2/1987 | Comte | 174/119 R |
| 4,671,848 | 6/1987 | Miller et al. | 156/643 |
| 4,711,027 | 12/1987 | Harris | 29/869 |
| 4,761,535 * | 8/1988 | Lawson | 219/121.68 |
| 4,818,322 | 4/1989 | Morino et al. | 156/272.8 |
| 4,840,186 | 6/1989 | Lekholm et al. | 607/116 |
| 4,931,616 | 6/1990 | Usui et al. | 219/121.68 |
| 4,970,367 | 11/1990 | Miller | 219/121.68 |
| 5,057,661 | 10/1991 | Banner | 219/56.22 |
| 5,113,574 | 5/1992 | Nuss | 29/597 |

(List continued on next page.)

FOREIGN PATENT DOCUMENTS

| | | | |
|---|---|---|---|
| 1146228 | 5/1983 | (CA) | 337/70 |
| 656316A5 | 6/1996 | (EP) | B67C/3/20 |
| 59-127984 * | 7/1984 | (JP) . | |
| 62-2544441 | 11/1987 | (JP) | H01L/21/60 |
| 171584 | 3/1989 | (JP) | 219/121.85 |
| 5-337672 * | 12/1993 | (JP) | 219/121.74 |
| 7-7825 * | 1/1995 | (JP) . | |
| 8-265931 * | 10/1996 | (JP) . | |
| 8002231 | 4/1980 | (WO) | A61N/1/04 |
| 8304182 | 5/1983 | (WO) | A61N/5/04 |
| 8807431 | 3/1988 | (WO) | B25K/26/00 |

OTHER PUBLICATIONS

"IBM Technical Disclosure Bulletin, 12(12)", p. 3794, (May, 1971).

Derwent Abstract of USSR Patent document No. 949, 746, published Aug. 7, 1982.

Primary Examiner—Geoffrey S. Evans
(74) Attorney, Agent, or Firm—Schwegman, Lundberg, Woessner & Kluth, P.A.

(57) ABSTRACT

An apparatus for using a laser beam to remove or ablate an insulating coating from a desired segment of an insulating coating from a desired segment of an insulated conductor (wire) without damaging or causing mechanical stress to the wire. A lens can be used to focus the laser beam at a focal point and a support to locate the insulated conductor in a position between the lens and the focal point in a path of the laser bean. A reflector can be aligned with the opening so as to reflect the laser beam portion back toward the conductor. The support can include a generally planar coil guide such as a Y-shaped groove.

38 Claims, 5 Drawing Sheets

U.S. PATENT DOCUMENTS

| | | | |
|---|---|---|---|
| 5,298,715 | 3/1994 | Chalco et al. | 219/121.64 |
| 5,458,629 | 10/1995 | Baudino et al. | 607/116 |
| 5,524,338 | 6/1996 | Martynuik et al. | 29/825 |
| 5,534,022 | 7/1996 | Hoffmann et al. | 607/122 |
| 5,569,398 | 10/1996 | Sun et al. | 219/121.68 |
| 5,580,699 | 12/1996 | Layman et al. | 430/311 |
| 5,837,961 | 11/1998 | Miller et al. | 219/121.68 |
| 5,845,396 | 12/1998 | Altman et al. | 29/885 |

\* cited by examiner

APPARATUS FOR REMOVING AN INSULATING LAYER FROM A PORTION OF A CONDUCTOR

This application is a Divisional of U.S. application Ser. No. 08/744,239 filed Nov. 5, 1996, now issued as U.S. Pat. No. 5,935,465, the specification of which is hereby incorporated by reference.

TECHNICAL FIELD OF THE INVENTION

The present invention relates generally to implantable medical devices and to electrically conductive portions thereof. More specifically, the invention relates to the leads of an implantable medical device that conduct electricity from the power source of the device to the target tissue. Still more specifically, the present invention facilitates production of such leads by providing an apparatus and device for selectively stripping individual conductors in a multi-conductor lead without damaging the individual conductors, and enables multiple connections to be made to a lead without requiring separation of its individual wires.

BACKGROUND OF THE INVENTION

A pacemaker (or "pacer" as it is commonly labeled) is an implantable medical device which delivers electrical pulses to an electrode that is implanted adjacent or into the patient's heart in order to stimulate the heart so that it will beat at a desired rate. A normal human heart contains a natural pacemaker by which rhythmic electrical excitation is developed. If the body's pacemaker performs correctly, blood is oxygenated in the lungs and efficiently pumped by the heart to the body's oxygen-demanding tissues. However, when the body's natural pacemaker malfunctions, due to age or disease, an implantable pacemaker often is required to properly stimulate the heart. An in-depth explanation of certain cardiac physiology and pacemaker theory of operation is provided in U.S. Pat. No. 4,830,006.

Pacers and other implantable electrical stimulation devices generally comprise a power source and at least one lead extending from the power source to the point of stimulation An implanted lead must be capable of conforming to the body in which it is implanted. In addition, an implanted lead is subject to repeated flexing due to heartbeat, breathing or other body movements. Pacing leads, which are attached to the myocardium, are particularly subject to rigorous and continuous flexing. Improvements in pacemaker technology have increased the life of the devices and thus increased the period for which a lead is expected to operate without failure. It has been estimated that, in a 10-year period, a pacemaker lead must withstand over 360,000,000 flexes. Therefore, the most successful leads are those that flex easily and are resistant to fatigue. Because leads must transmit electrical current from a limited power source, it is also desirable to provide leads that have low electrical resistance.

In addition, although early pacers included a single remotely-positioned electrode and therefore relied on conduction through the surrounding body to complete the circuit, newer pacers typically include a bipolar lead terminating in two, spaced-apart electrodes. This reduces the resistance of the circuit and thus reduces power consumption through $I^2R$ losses, as most of the circuit is comprised of metal conductors, rather than through the surrounding tissue. Other of technologies have been developed that also require the placement of one or more electrodes or other devices in the heart. These include various devices that sense the state of the heart so as to optimize pacing, such as temperature sensing thermocouples and photo-oxymetry devices. Often, two or more of these devices are connected to the pacer by a single, multi-fillar lead. Typically, the number of fillars corresponds to the number of electrodes or other devices, but instances in which two or more fillars are electrically connected to a single electrode or other device are also common. Each conductor in a multi-fillar lead must be insulated from the other conductors and from the environment in which it is implanted.

Substantial effort has been employed in the development of specialized, multi-fillar leads that optimize the characteristics of flexibility and electrical conductivity while providing a surface that is suitable for implantation and that is able to resist the corrosive environment within a living body. An example of one such multi-fillar lead is described in U.S. Pat. No. 4,840,186 to Lekholm et al. It has been common to include either an electrically insulating sheathing layer, such as that disclosed in U.S. Pat. No. 4,640,983 to Comte, or to insulate individual conductors separately, as disclosed by Lekholm. Lekholm also teaches a second, additional insulating layer, in which the individually insulated conductors are embedded.

Another type of multi-fillar lead has two or more individually insulated conductors that are wound into coaxial helical coils having a uniform inner diameter. These conductors can have the same or different diameters. An example of such a lead is disclosed in U.S. Pat. No. 4,640,983. The insulation is typically made of a Teflon-type material or of a silicon-based material, or similar suitable insulating material such as are known in the art. It has been found that coiling the conductors in this manner allows the conductors to provide mutual mechanical support that further extends the life of each conductor.

Because the individual conductors in a multi-pole lead typically need to be connected to electrodes that are some distance apart, it is necessary to terminate each conductor separately. Electrical connection to an electrode or other device is made by mechanically stripping the insulation from the end of each conductor at the point where it is desired to attach an electrode. However, the act of mechanical stripping damages the wire and results in residual stresses, which shorten the life of the conductor. In addition, the step of uncoiling coiled wires from each other as required in conventional stripping procedures is time-consuming and labor-intensive and may itself result in damage to the wires. Therefore, it is desirable to provide a technique for stripping the wire non-mechanically.

Furthermore, because the most commonly used mechanical equipment uses an axial stripping process, stripping can only occur adjacent a wire end. Therefore, each conductor typically terminates at an electrode so as to avoid having a length of stripped conductor extend beyond the electrode. In order to ensure that the electrodes are spaced apart when the lead is implanted, one conductor or fillar is made shorter than the other. In these instances, where one conductor of a multi-fillar lead terminates and the remaining conductor extends beyond the first, the extending portion of the longer conductor is not mechanically supported against flexure to the degree that the conductors are mutually supported along the body of the lead. While it is theoretically possible to attach a mechanical support for the extending conductor segment so as to replace the terminated conductor in this region, each such connection or discontinuity decreases reliability of the device and increases manufacturing costs. Therefore, it is desirable to provide a technique for stripping a limited segment of one conductor at some distance from its terminal end in a manner that allows both wires to retain their individual insulation at points beyond the first electrode and extend all the way to the end of the lead, thereby providing reliable mechanical support for the longer lead in this region. While the foregoing discussion is presented in terms of a bi-fillar conductor, it will be understood that the same principles apply in multi-fillar leads having more than two conductors.

In addition, from a manufacturing standpoint, it would be most preferable to strip the wires without first having to uncoil them, so as to avoid the mechanical damage caused by the uncoiling and recoiling processes and to avoid the costly labor intensive steps associated therewith. It is desirable to strip only one wire in a given lead segment, as electrical contact between conductors would result in short circuiting. In order to avoid stripping more than one wire when multiple wires are coiled together, therefore, it is necessary to provide an apparatus and technique that can selectively strip one of several adjacent wires in a multi-wire coil.

SUMMARY OF THE INVENTION

Oour invention relates to an apparatus and technique for stripping an insulating coating from a conductor without damaging the conductor, and for selectively stripping an insulating coating from a individual conductors in a multi-conductor coil. A laser beam formulated to ablate the insulating coating is directed at the portion of the wire from which it is desired to remove the insulation. Because no mechanical force is used and the conductor is not deformed in the process, the present technique causes no damage to the conductor. Because the insulation layer ablates well before significant energy is transferred to the conductor, the present technique has no permanent effect on the conductor. In a multi-conductor coil in which the insulating layers on the individual conductors are the same, selective stripping is accomplished by uncoiling the conductors, stripping the desired portion of each and recoiling the conductors, if desired.

Alternatively, in a multi-conductor coil, the insulating coating on some of the individual conductors can differ from that on others of the conductors, such that a laser beam can be employed to selectively cause the ablation of one coating without causing the ablation of other coatings. Because the insulation removal method is selective, it is not necessary to uncoil the multiple conductors from one another. The insulating layers on individual conductors may differ in their physical properties, such as melting point or thermal absorption, or may differ in color or thickness, so as to render them selectable.

A device is disclosed that uses a laser beam to completely strip the insulating layer from a desired segment of a conductor. The device includes means for directing the laser beam at one side of a predetermined segment of the conductor and at least one reflector for directing a portion of the laser beam toward the opposite side of the same segment.

BRIEF DESCRIPTION OF THE DRAWINGS

Other objects and advantages of the invention will become apparent upon reading the following detailed description and upon reference to the accompany drawing in which.

DETAILED DESCRIPTION OF THE INVENTION

Although the apparatus and method of the present invention are described generally in terms of a bipolar pacer for stimulation of a heart, it will be understood that the present invention extends to other devices that utilize implantable leads. Other types of electrical devices that include implantable leads include implantable defibrillators and neurostimulators. Furthermore, although the present invention is described for simplicity in terms of a lead comprising two conductors, it will be understood that it has equal applicability in the context of single pole leads and multi-pole leads having more than two conductors.

Figure 1:
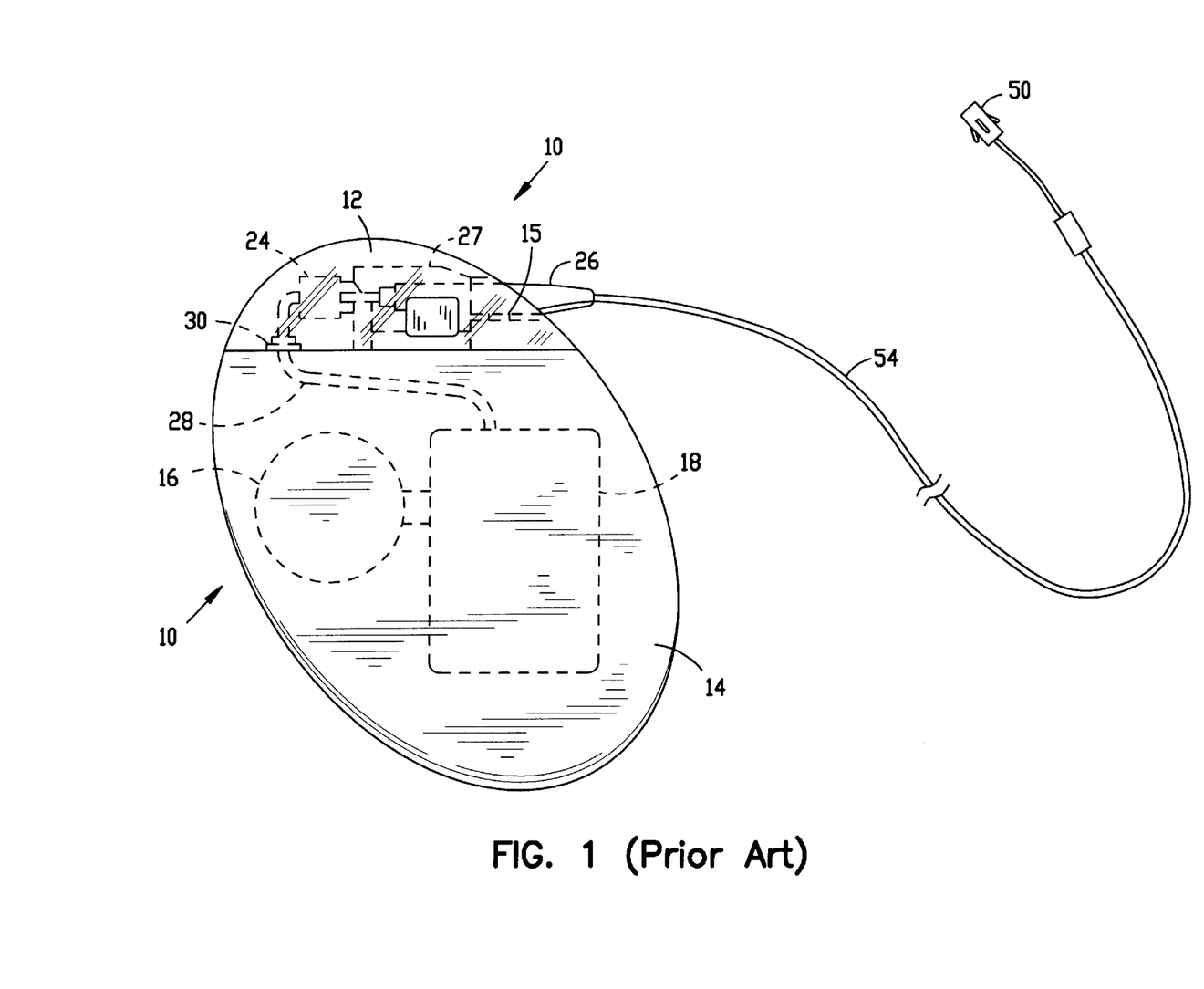
FIG. 1 is an example of a pacer having a multi-pole lead constructed according to the prior art.

Referring initially to FIG. 1, there is shown a typical implantable device 10 which, in the embodiment shown in FIG. 1, is adapted for use as a self-contained implantable cardiac pacer. Pacer 10 comprises a header 12 and a can or housing 14. Housing 14 contains an electrical energy source, such as battery 16, and a microprocessor 18 for transmitting and receiving electrical signals and for generating an electrical pulse to stimulate a patient's heart in a predetermined manner. Header 12 includes a single chamber or bore 15. An electrical terminal 24 is located at the inboard end of bore 15 and is electrically connected to the microprocessor 18. Header 12 is molded or glued to housing 14 and serves as a termination point for the electrical conductors that are used to transmit electrical signals, including the generated pulse, to and from the patient's heart.

Pacer can 14 is made of a biocompatible, corrosion-resistant metal such as stainless steel or titanium. The header 12 is typically mounted on housing 14 after the microprocessor 18 and battery 16 are assembled within the interior of the housing and the housing 14 is welded shut. Terminal 24 and other components in header 12 are potted in cured resin, which surrounds and insulates all of the components. Use of a transparent resin further allows observation of the components housed therein. Header 12 may be formed from any of a large number of biocompatible materials capable of retaining and insulating terminal 24. For many applications, header 12 preferably is made of an epoxy resin or similar thermosetting polymer material that is cured in situ over terminal 24. In addition to epoxy, other material suitable for header 12 include glass, plastics, elastomers such as Dow Chemical's Pellethane and ceramic materials such as sapphire.

Still referring to FIG. 1, a conventional bipolar pacer includes a pair of electrodes 50, 52 that are used to stimulate the heart. Electrodes 50, 52 are interconnected with pacer 10 via conductors (FIG. 2) that form a flexible lead 54. The proximal ends of the conductors electrically interconnect electrodes 50, 52 with the pulse generation circuitry contained in microprocessor 18 and are insulated within a covering 26, preferably comprising silicone rubber. The near end of lead 54, including covering 26, is received in bore 15 and the conductors are connected to terminal 24. The elements used to interconnect external electrodes 50, 52 with terminal 24 and thereby with circuitry within pacer 10 are conventional and well understood by those skilled in this art. Further details concerning such interconnections are shown, for example, in U.S. Pat. Nos. 5,076,270, 4,640,983 and 4,860,750.

Figure 2:
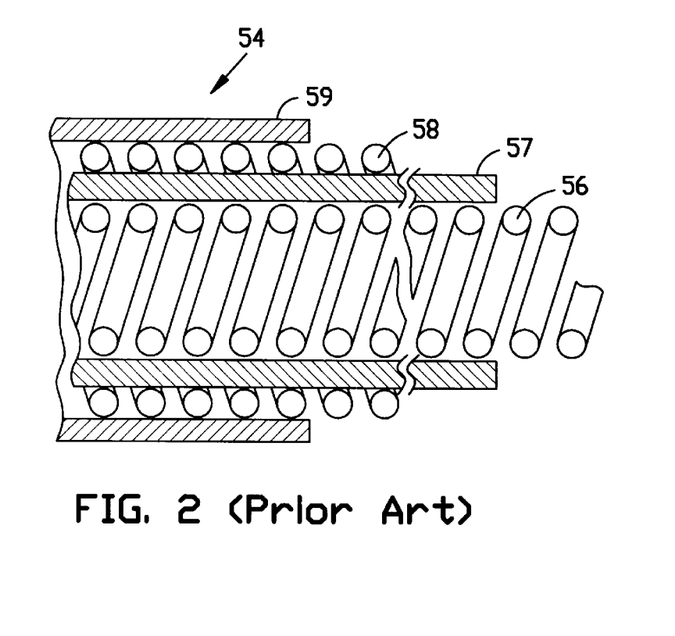
FIG. 2 is an enlarged cross-sectional view of the bi-fillar lead of FIG. 1.

Referring now to FIG. 2, a conventional bipolar lead 54 such as might be used to connect electrodes 50 and 52 to pacer 10 comprises a first conducting coil 56 and a second conducting coil 58. Coils 56 and 58 are coaxial along most of their lengths, with the outer diameter of coil 56 being less than the inner diameter of coil 58. Coils 56 and 58 are not individually insulated and short circuiting between them is prevented by the insertion therebetween of an insulating tube 57 having a lumen in which coil 56 is received. An insulating sheath 59 is provided outside of coil 58 to electrically insulate coil 58 and protect it from the corrosive effects of the body environment. Alternatively, the conductors can be straight wires that are positioned in separate lumens of a multi-lumen insulating tube. It is a known disadvantage of this technique that, as there is only one layer of insulation between the conductors, a single defect or tear in that layer can cause short-circuiting.

Electrodes 50, 52 are typically some distance apart. In the instance of a conventional multi-pole lead 54 in which one or more conductors are located within an outer conductor and separated from one another by an insulating tube 57, exposure of two or more spaced-apart electrodes is accomplished by terminating the outer conductor at a point some distance from the end of the inner conductor(s), allowing the inner conductor(s) to extend beyond the first termination and providing an electrode (not shown) on each of the successive conductor terminations. For this reason, electrode 52 is commonly referred to as the "ring electrode," while electrode 50 is commonly referred to as the "tip electrode." Depending on the construction of the lead, the formation of separate electrodes may be more or less difficult, however, construction of leads in this manner is generally well known in the art.

Figure 3:
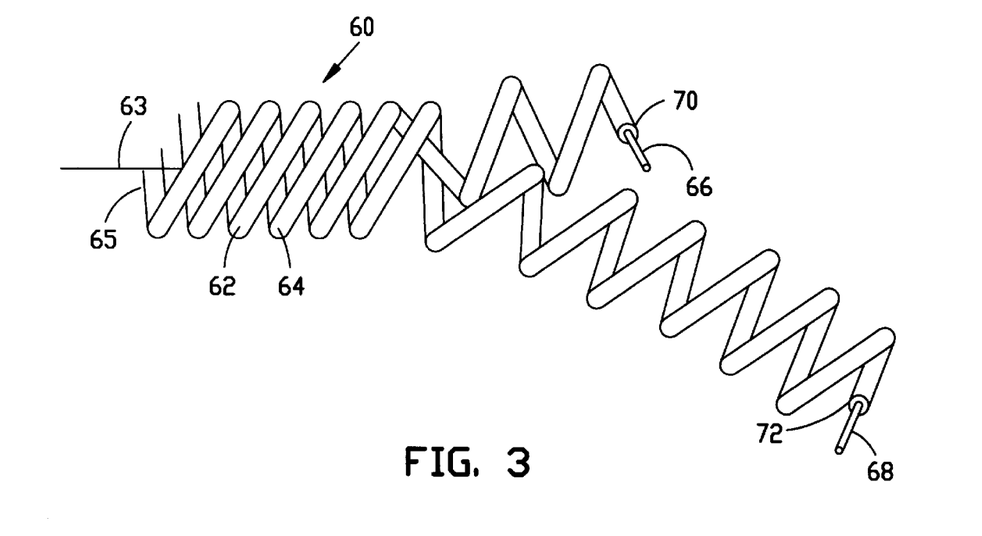
FIG. 3 is an enlarged perspective view of a bi-fillar conductor to which the present invention is applicable.

Referring now to FIG. 3, a lead 60 constructed according to the present invention comprises two or more flexible and resilient coils 62, 64 wound in the same direction around a common axis 63. According to a preferred embodiment, coils 62 and 64 have substantially the same inside diameter and are coaxially wrapped in parallel. The space at the center of coils 62, 64 defines a lumen 65. Coils 62, 64 each preferably comprise an inner, conducting wire 66, 68 respectively, and an outer, electrically insulating layer 70, 72. Conducting wires 66, 68 are each preferably drawn filled tube or drawn braided multi-strand wires, and are both sufficiently conductive and resilient enough to withstand repeated flexing. Insulating layers 70, 72 preferably comprise a flexible, biocompatible material such as silicone, tetrafluoroethylene or polyurethane. The specific properties of insulating layers 70, 72 that form a part of the present invention are set forth in detail below. It is preferred to provide conducting wires that are individually insulated for the reasons discussed below and because individual insulation provides redundant, and therefore more reliable, insulation against electrical short circuiting between adjacent conductors.

As discussed generally above, the typical prior art method for attaching an electrode to an electrically insulated wire includes mechanically stripping the insulating layer from the end of the wire. In order to perform such a process on the preferred lead 60 shown in FIG. 3, it is necessary to uncoil coils 62, 64 from one another over a short distance at one end. The ends of the two separate wires are then inserted into a conventional mechanical stripping device, which removes the insulating layer 70, 72 from a short region adjacent each wire end, thereby providing an exposed length of each conducting wire 66, 68, to which the electrodes can be attached. This process has several disadvantages. As described above, one wire is typically shortened, so that the electrodes on each wire end are spaced apart, with the result that the longer wire is deprived of the mechanical support of the second conductor. In addition, both the uncoiling and the mechanical stripping processes can damage the wire and reduce its useful life. Lastly, in the context of manufacturing large numbers of implantable leads on a commercial scale, the time and labor required to accomplish these steps become a significant portion of the manufacturing cost.

Figure 4:
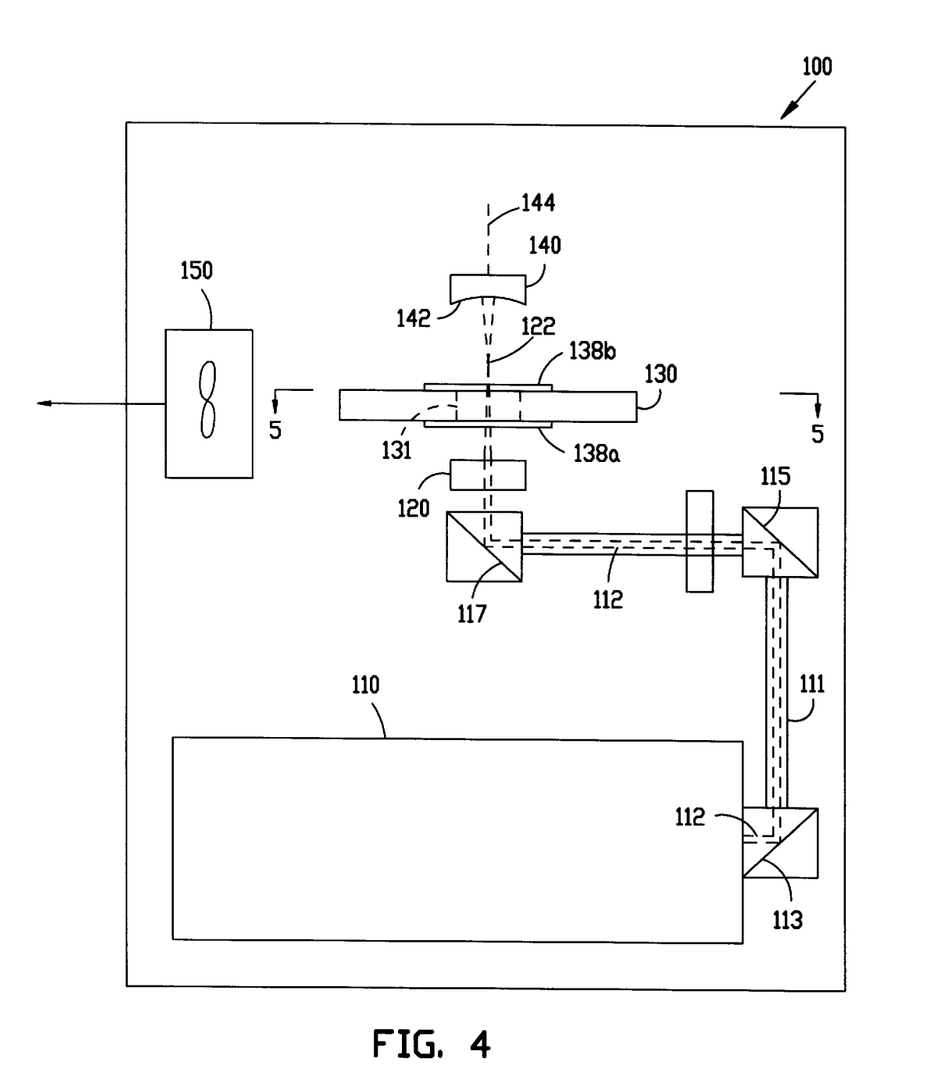
FIG. 4 is a schematic diagram showing a front view of the components of a laser stripping apparatus constructed in accordance with the principles of the present invention and capable of selectively stripping insulation from the conductor shown in FIG. 3.

The present invention provides a method and apparatus that avoids many of these issues. Referring now to FIG. 4, a laser pulsing device 100 that quickly and effectively removes insulation from an insulated wire is represented schematically. Device 100 is capable of removing the insulating layer from a wire without requiring that the wire terminate adjacent the stripped portion. Device 100 includes a laser source 110, a focusing lens 120, a wire-supporting pallet 130, and a reflector 140.

Laser source 110 preferably comprises a $CO_2$ laser, such as an IMPACT® laser available from Lumonics Inc., 105 Schneider Road, Kanata (Ottawa) Ontario, which emits a beam 112 having a cross-sectional area approximately 12 mm×12 mm. The preferred operating power is 70 W, although the above device has a maximum power output of approximately 5 MW. After exiting laser source 110, beam 112 is deflected by a series of turning mirrors 113, 115, 117, which position and orient the beam in the desired manner. Guide tubes 111 contain the beam path. As shown, mirrors 113, 115, and 117 position the beam so that it passes across a desired working region in which pallet 130 is located. After reflecting off mirror 117, beam 112 passes through focusing lens 120. The focal length of lens 120 is preferably, but not necessarily, on the order of about 2 to 25 inches. The beam transmitted by lens 120 crosses pallet 130 and reflects off reflector 140. Reflector 140 is preferably somewhat concave, so that the reflected beam is refocused in the return direction, as shown.

Wire-supporting pallet 130 is preferably, but not necessarily, positioned normal to beam 112 between lens 120 and its focal point 122, so that the laser beam is not completely focused as it passes through the pallet 130. At the point where beam 112 crosses the pallet 130, the dimensions of the beam 112 are preferably approximately 4 mm×4 mm. Reflector 140 preferably comprises a parabolic mirror 142 having an axis 144 that is parallel to and coincidental with beam 112. A mechanism (not shown) is provided for moving pallet 130 laterally across the beam 112 so as to allow ablations at multiple points on a single lead without requiring movement of the laser beam. While this technique is preferred because of its relative simplicity, it will be understood that other techniques, such as movement of the laser beam, are contemplated within the scope of the present invention.

Figure 5:
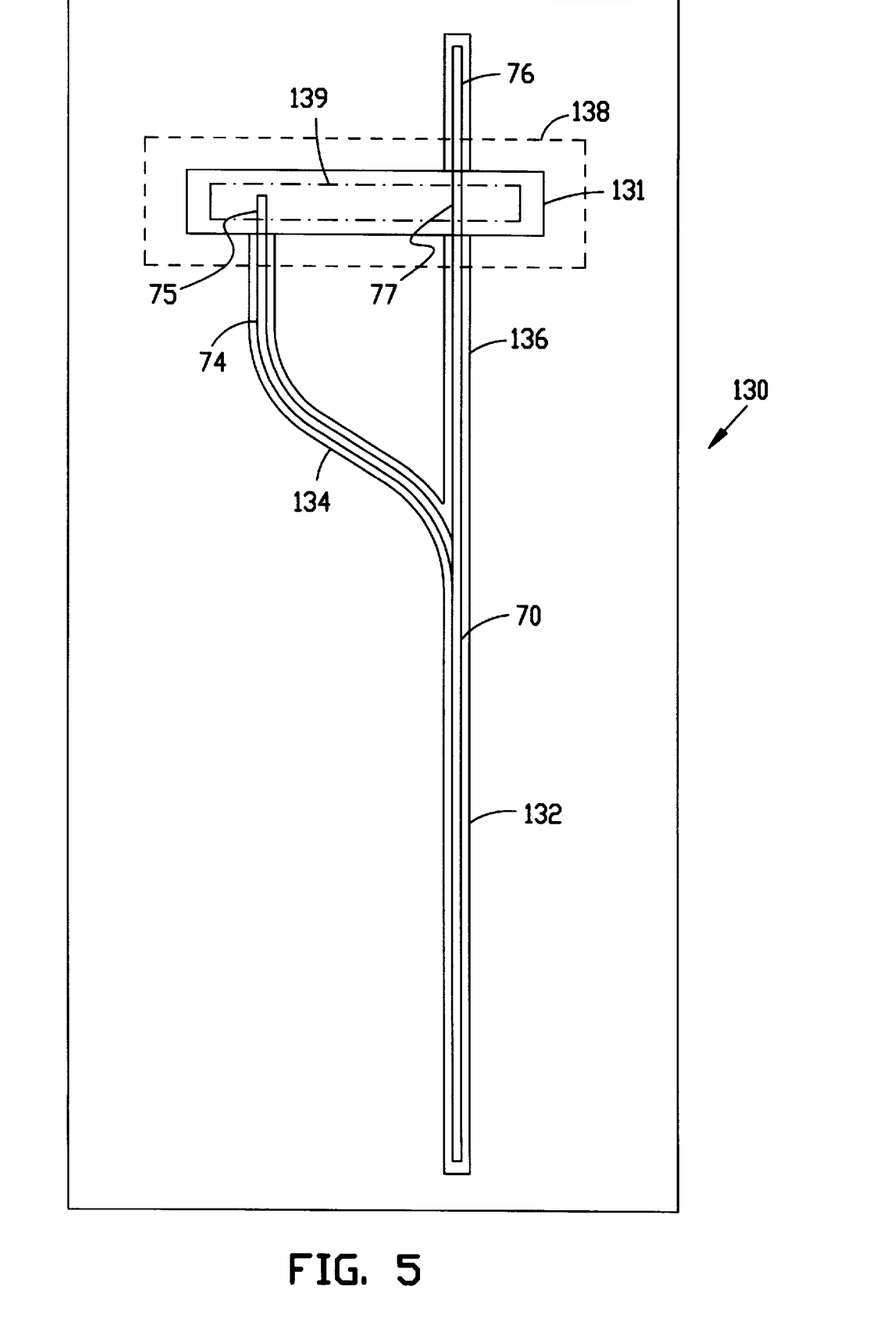
FIG. 5 is a plan view of a wire supporting pallet taken along lines 5—5 in FIG. 4.

Referring now particularly to FIG. 5, pallet 130 comprises a generally planar support tray that includes an opening 131 therethrough and three grooves or channels 132, 134, 136 in its upper major surface. Channels 132, 134, 136 preferably, but not necessarily, lie in a single plane. According to a preferred embodiment, channels 132, 134, 136 generally define a "Y" shape. Main guide channel 132 is adapted to receive a lead, such as lead 60 described above, that comprises two coaxially coiled conducting wires 62, 64. A first minor channel 136 is generally a continuation of main channel 132, while second minor guide 134 departs from channel guide 132 at a tangent and curves around to assume a course generally parallel to main guide 132. As most leads are in the range of 10–25 inches (20–60 cm), pallet 130 is preferably sized to accommodate leads of this size.

Referring now to FIGS. 4 and 5, at least one mask 138 having an opening 139 therethrough is preferably used in conjunction with pallet 130 (shown in phantom in FIG. 5). Mask 138 comprises a sheet of any suitable opaque material. Opening 139 in mask 138 is preferably smaller than opening 131 in pallet 130. Mask 138 overlays pallet 130 so that exposure of the supported lead to laser beam 112 is limited to that portion of the lead that is exposed at opening 139. In this manner, mask 138 ensures that any stripping of the insulating layer from the lead coils is limited to a predetermined desired area. According to a preferred embodiment, a mask 138 is provided on each side of pallet 130, so that one mask 138a lies between lens 120 and pallet 130 and one mask 138b lies between reflector 140 and pallet 130 (FIG. 4). Masks 138a–b can be retained in their desired positions relative to pallet 130 by any suitable means, such as clips or clamps. In this manner, light impinging on pallet 130 from either lens 120 or reflector 140 is intercepted by a mask, with the exception of light passing through openings 139.

Referring still to FIG. 4, the laser stripping equipment is preferably sealed so as to contain any noxious gases that might be emitted during ablation of the insulating layer. An exhaust system 150 is included that provides a stream of clean dry air flowing in a direction generally perpendicular to beam 112 and parallel to the plane of pallet 130. It is preferred to maintain a stream of clean dry air on the area to be stripped. The flowing air removes debris, keeps the lens 120 clean and flushes the exhaust gases from the system.

Referring again to FIG. 5, in operation, a bi-fillar lead 70 is separated into its component coils 74, 76 along a portion of its length adjacent one end and the separated coils 74, 76 are each placed into minor guides 134, 136, respectively. The un-separated portion of lead 70 is received in guide 132. Masks 138a–b are positioned on each side of pallet 130 and over coils 74, 76 in grooves 134, 136 such that mask openings 139 are aligned with each other and with opening 131 in pallet 130 and pallet 130 is positioned so that at least one of coils 74 and 76 is supported across the aligned openings. A laser beam comprising multiple pulses, at a frequency determined by laser source 110, is emitted from laser 110 and reflected along the path described above as laser beam 112. The frequency of the preferred laser described above is 150 Hz and the beam is preferably comprised of approximately 20–30 pulses, each less than 10 msec long. It will be understood that these are preferred values for only embodiment and the beam to which a conductor is exposed may vary substantially in duration, frequency and number of pulses, depending on the nature of the insulating layer being removed.

Figure 6:
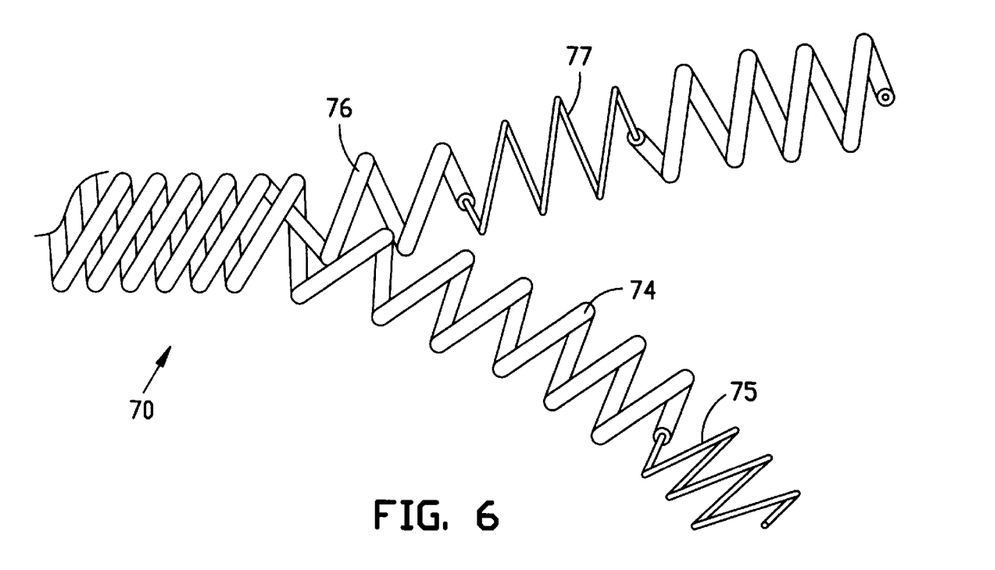
FIG. 6 is a enlarged perspective view of a bi-fillar conductor having an uncoiled section to which the process of the present invention has been applied.
Figure 7:
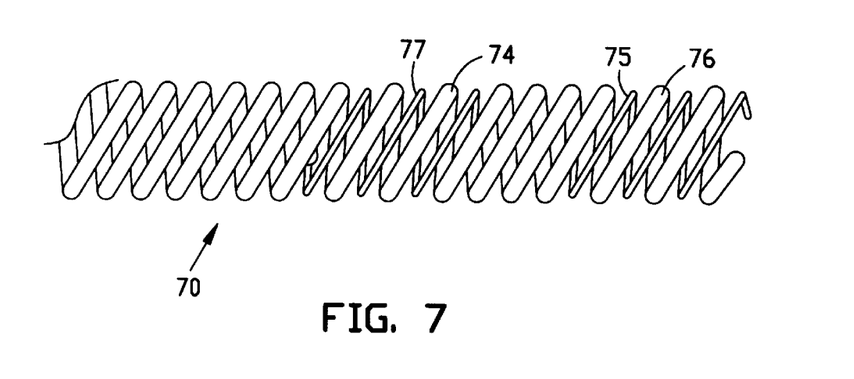
FIG. 7 is a enlarged perspective view of the bi-fillar conductor of FIG. 6 after it has been re-coiled.

As it passes through lens 120, beam 112 is focused at a point some distance beyond the plane of pallet 130. Some of beam 112 may be absorbed by pallet 130 and/or mask 138a. The portion of beam 112 passing through openings 139 and 131 ablates the insulating coating from one side of the exposed coil. Sufficient light is transmitted past the coil 74 (or 76) and reflected back toward the opening by reflector 140 that the insulating coating is virtually simultaneously ablated from the opposite side of the exposed coil. A preferred light beam has an energy of 70 W at 150 Hz, which allows the beam to completely remove the insulating coating using this technique without damaging either the conductor within the coil or the stripping equipment. Thus, a method is provided for removing an insulating coating without terminating the coil and without mechanically damaging or deforming the conducting wire inside the coil. The position of pallet 130 is then shifted laterally in its plane so that the second conductor is moved into the path of the laser beam. Because of the offset in groove 134, if the laser beam is applied at points corresponding to openings 139 in masks 138a–b, it will strip a portion 75 of conductor 74 at a point adjacent its end and a portion 77 of conductor 76 at a point remote from its end, as shown in FIG. 6. According to one preferred embodiment, a lead 70 that has been stripped in this manner is removed from pallet 130 and coils 74, 76 are re-coiled coaxially, leaving the two stripped portions 75, 77 as electrical connections that are spaced apart along the axis of the lead, as shown in FIG. 7. This technique allows the coil associated with the near electrode (76) to extend beyond its electrode attachment without mechanical damage. Thus, both conductors can extend as far as the second, remote electrode and thereby provide the same mutual mechanical support that they provide over the length of the lead. To avoid shorting between the first and second conductors at the remote end, the conductor connected to the near electrode is terminated in insulation in the housing or "boot" of the remote electrode (not shown).

It will be understood that the laser stripping apparatus can be modified in various ways without departing from the spirit of the invention. For example, the laser beam itself can be split or two (or more) beams could be provided, so that the multiple conductors comprising a lead can be stripped simultaneously. In such a configuration, the reflectors need not reverse the direction of the laser beam as described above, and could instead each be angled to reflect the beam onto another conductor.

Also, it will be understood that the technique described above can be modified to create leads containing more than two conductors by modifying the configuration of the grooves in pallet 130. It will further be understood that the configuration of pallet 130 can be modified from that disclosed without departing from the scope of the present invention. Pallet 130 is merely a vehicle and means for supporting a lead during the ablation step. Therefore, the present invention contemplates any pallet configuration that provides suitable support and enables the desired stripping to occur.

Further according to the present invention, the need to separate or uncoil the individual coils that form a lead can be avoided by providing individual conductors with insulating coatings that are affected differently by the laser beam. For example, differences in sensitivity to the laser beam can be achieved by providing insulating coatings having different colors, different thicknesses, different chemical additives or different melting points.

It has been found that darker colored insulation layers absorb more energy from the laser beam and therefore ablate more quickly. Similarly, thicker layers require more energy to achieve ablation than do relatively thin layers. Thus, if one coil is provided with a relatively dark or thin coating and the second coil is provided with a relatively light or thick coating, the lead can be subjected to laser ablation without first separating the coils. Because the darker (or thinner) layer will be ablated before the lighter (or thicker) layer, the conducting surface of the first coil can be exposed while still maintaining the insulating coating on the second conductor. Although the insulating coatings of both conductors will ablate under conditions that ablate the darker (thinner) conductor, short-circuiting can be avoided by terminating the first conductor in the boot adjacent the second electrode.

Alternatively, the coatings themselves can comprise different materials altogether, such as tetrafluoroethylene-based and silicon-based insulations, and/or different types of lasers can be used to provide beams having differing ablation characteristics. For example, in a bi-fillar lead, one conductor can be coated with a tetrafluoroethylene-based insulation and the second conductor can be coated with a silicon-based insulation. These coatings respond differently to different laser beam types, so individual coils in a bi-fillar lead can be individually ablated without being first uncoiled from each other.

Similarly, the individual conductor coatings can be made of different molecular weight polymers or can include additives such as wavelength-specific absorbents and/or additives that respond differently to various pre-treatments, such as exposure to microwaves, so that the pre-treated coils are differently pre-disposed to ablation prior to contact with the laser beam. The foregoing disclosure is intended to be illustrative only and is not exhaustive of the variations contemplated for use in accordance with the techniques described herein.

When it is desired to check or calibrate the laser ablation equipment, light-sensitive paper can be used with the pallet and/or the mask to get feedback necessary for calibration of the laser stripper. In this manner, the laser beam can be positioned and aligned very precisely. Calibration of equipment in this manner is common practice in the field of laser assisted processing.

While preferred embodiments of this invention have been shown and described, modifications thereof can be made by one skilled in the art without the departing from the spirit or teaching of this invention. The embodiments described herein are exemplary only and are not limiting. Many variations and modifications of the system and apparatus are possible and are within the scope of the invention. For example, although the invention is described generally in terms of a pacer connected to a heart by means of a bipolar lead, it will be understood that that it extends to other types of implantable multipolar leads in which the separation of connections is relevant. Accordingly, the scope of the protection is not limited to the embodiments described herein, but is only limited by the claims which follow, the scope of which shall include all equivalence of the subject matter of the claims.

What is claimed is:

1. Am apparatus for removing an insulating layer from a portion of a conductor that is sheathed in the insulating layer without damaging the conductor, comprising:

a laser beam source for emitting a laser beam;

a lens for focusing the laser beam at a focal point; and a support to locate the conductor in a position between the lens and the focal point in a path of said laser beam, wherein said support includes a generally planar coil guide.

2. The apparatus according to claim 1 wherein said support is configured to allow passage of at least a portion of said laser beam beyond said support.

3. The apparatus according to claim 2 wherein said support includes an opening therethrough to allow the passage of at least a portion of said laser beam.

4. The apparatus according to claim 2, further including a reflector positioned in the path of said laser beam beyond said processing position and aligned so as to reflect said laser beam portion.

5. The apparatus according to claim 4, wherein said reflector reflects said laser beam portion back toward said conductor.

6. The apparatus according to claim 4 wherein said reflector is concave.

7. The apparatus according to claim 1, wherein the lens is located between said laser beam source and said support.

8. The apparatus according to claim 7 wherein said lens focuses said laser beam at a point between about 2 inches to about 25 inches beyond the lens.

9. The apparatus according to claim 1 wherein the insulating layer is completely removed from the conductor portion by the laser beam.

10. The apparatus according to claim 1 wherein said generally planar coil guide includes a groove.

11. The apparatus according to claim 1, wherein said coil guide comprises a generally Y-shaped groove.

12. The apparatus according to claim 11 wherein said Y-shaped groove comprises a substantially straight main guide and two minor guides and one of said minor guides is an extension of said major guide.

13. The apparatus according to claim 1 further including means for moving said support through said beam.

14. The apparatus according to claim 1 further including means for moving said beam across said support.

15. The apparatus of claim 1, further comprising a reflector positioned in the path of the laser beam, the focal point located between the conductor and the reflector.

16. The apparatus of claim 1, wherein the focal point is located between about 2 inches to about 25 inches beyond the lens.

17. An apparatus for removing an insulating layer from a portion of a conductor that is sheathed in the insulating layer without damaging the conductor, comprising:

a laser beam source for emitting a laser beam;

a support for supporting the conductor in a desired position, said support including an opening to allow the passage therethrough of at least a portion of said laser beam, and wherein said support includes a generally planar coil guide;

a beam orienting apparatus directing said laser beam onto the conductor portion, said beam orienting apparatus including a lens positioned between said laser beam source and said conductor, said lens focusing said laser beam at a point somewhat beyond said conductor;

a reflector aligned with said opening so as to reflect said laser beam portion back toward said opening.

18. The apparatus according to claim 17 wherein said reflector is concave.

19. The apparatus according to claim 17 wherein a focal point of the lens is located between the conductor and the reflector.

20. The apparatus according to claim 17 wherein a focal point of the lens is between about 2 inches to about 25 inches beyond the lens.

21. The apparatus according to claim 17 wherein said generally planar coil guide includes a groove.

22. An apparatus for removing an insulating layer from a portion of a conductor, the apparatus comprising:

a laser beam source for emitting a laser beam;

a support to locate the conductor in a desired processing position in a path of said laser beam, wherein said support includes a generally planar coil guide; and a lens between said laser beam source and said support, wherein said lens focuses said laser beam at a point beyong said conductor.

23. The apparatus of claim 22, wherein said support is configured to allow passage of at least a portion of said laser beam beyond said support.

24. The apparatus according to claim 22, wherein said support includes an opening therethrough to allow the passage of at least a portion of said laser beam.

25. The apparatus according to claim 22, further including a reflector positioned in the path of said laser beam beyond said processing position and aligned so as to reflect said laser beam portion.

26. The apparatus according to claim 25, wherein said reflector reflects said laser beam portion back toward said conductor.

27. The apparatus according to claim 25 wherein said reflector is concave.

28. The apparatus according to claim 22 further including means for moving said support through said beam.

29. The apparatus according to claim 22 further including means for moving said beam across said support.

30. The apparatus of claim 22, further comprising a reflector positioned in the path of the laser beam, the focal point located between the conductor and the reflector.

31. The apparatus of claim 22, wherein the focal point is located between about 2 inches to about 25 inches beyond the lens.

32. An apparatus for removing an insulating layer from a portion of a conductor that is sheathed in the insulating layer without damaging the conductor, comprising:

a laser beam source for emitting a laser beam; and a support to locate the conductor in a desired processing position in the path of said laser beam, said support including a generally planar coil guide.

33. The apparatus according to claim 32 wherein said coil guide comprises a generally Y-shaped groove.

34. The apparatus according to claim 33 wherein said Y-shaped groove comprises a substantially straight main guide and two minor guides and one of said minor guides is an extension of said major guide.

35. The apparatus according to claim 32 further including means for moving said support through said beam.

36. The apparatus according to claim 32 further including means for moving said beam across said support.

37. The apparatus of claim 32, wherein said support is configured to allow passage of at least a portion of said laser beam beyond said support.

38. The apparatus according to claim 32, wherein said support includes an opening therethrough to allow the passage of at least a portion of said laser beam.

* * * * *

UNITED STATES PATENT AND TRADEMARK OFFICE
CERTIFICATE OF CORRECTION

PATENT NO. : 6,326,587 B1
DATED : December 4, 2001
INVENTOR(S) : Cardineau et al.

Page 1 of 1

It is certified that error appears in the above-identified patent and that said Letters Patent is hereby corrected as shown below:

<u>Title page,</u>
Item [57], ABSTRACT
Lines 3-4, delete "an insulating coating from a desired segment of".
Line 8, delete "bean" and insert -- beam --, therefor.

<u>Column 9,</u>
Line 52, delete "Am" and insert -- An --, therefor.

Signed and Sealed this

Tenth Day of September, 2002

*Attest:*

JAMES E. ROGAN
*Attesting Officer*    *Director of the United States Patent and Trademark Office*